United States Patent [19]

Bogart et al.

[11] Patent Number: 4,883,475

[45] Date of Patent: Nov. 28, 1989

[54] CHEMICALLY TREATED PAPER PRODUCTS—TOWEL AND TISSUE

[75] Inventors: Larry Bogart, Penn Valley; James J. Hipkins, Prospect Park, both of Pa.; Morris L. Smith, Lawnside, N.J.

[73] Assignee: Scott Paper Company, Philadelphia, Pa.

[21] Appl. No.: 243,923

[22] Filed: Sep. 12, 1988

Related U.S. Application Data

[62] Division of Ser. No. 82,203, Aug. 6, 1987.

[51] Int. Cl.$^4$ ............................ A61K 7/40; A61K 7/48
[52] U.S. Cl. ...................................... 604/290; 604/312
[58] Field of Search ................................ 604/290, 312

[56] References Cited

U.S. PATENT DOCUMENTS 3,231,472  1/1966  Jacobi et al. ........................... 514/42
4,690,821  9/1987  Smith et al. ........................... 424/401

FOREIGN PATENT DOCUMENTS 2260612  9/1974  Fed. Rep. of Germany .

*Primary Examiner*—James C. Cannon
*Attorney, Agent, or Firm*—John A. Weygandt; John W. Kane, Jr.

[57] ABSTRACT

Disclosed are soft, absorbent and bulky cellulosic fibrous webs which have been treated so that they impart a soothing or emollient effect to the human skin when used for wiping or drying while essentially retaining their water-absorbent property and strength. The agent used in the present invention is a condensation product of an amino acid with a reducing sugar.

1 Claim, No Drawings

CHEMICALLY TREATED PAPER PRODUCTS—TOWEL AND TISSUE

This application is a division of application Ser. No. 082,203, filed Aug. 6, 1987.

BACKGROUND OF THE INVENTION

1. Field of the Invention

This invention relates to soft, absorbent and bulky cellulosic fibrous webs which have been treated so that they impart a soothing or emollient effect to the human skin when used for wiping or drying while essentially retaining their water-absorbent property and strength. The agent used in the present is a condensation product of an amino acid with a reducing sugar.

2. History of the Prior Art

It has heretofore been suggested to treat cellulosic fibrous webs with lanolin to impart a feeling of softness to the webs. See, for example, Wemyss, et al., U.S. Pat. No. 2,877,115 and Yang, U.S. Pat. No. 2,944,931 or with other fatty solids, see Britt, U.S. Pat. No. 3,305,392 However, such a treatment has the disadvantage that the water absorbency of the cellulosic web is dramatically reduced by the application of these fatty-type materials, so that the web can no longer satisfactorily perform a wiping or drying function in reference to moist skin.

SUMMARY OF THE INVENTION

The present invention has as its object rather than imparting the feeling of softness to cellulosic webs, the imparting to the human skin an emollient or soothing effect through wiping with a cellulosic web while retaining the drying and strength characteristics of the untreated web. In many environments such as hospitals and clinics, persons are required to frequently wash and dry their hands. This can produce skin irritation, particularly in cold weather. Also, persons suffering from the common cold must frequently apply facial tissues. Also people suffering from diarrhea must use large quantities of toilet tissue. Repeated wipings with treated toilet tissue has been found to condition the perineal region so that it maintains a non-irritating condition. Likewise, a soft feeling is achieved after using facial treatment in the manner of this invention so that the nasal skin is left with a velvety soft feeling even after repeated wipes.

The present inventors have found that the water absorbency can essentially be retained while imparting a skin soothing character to webs for drying or wiping the skin by treating soft absorbent cellulosic webs with glucose glutamate. Products made from such webs exhibit the ability to transfer chemicals from the cellulosic fibrous web to the skin generating emollient benefits while concomitantly successfully executing the previous function of the product which is to wipe or dry the skin. Webs treated with lanolin, by contrast, are markedly inferior in producing the desired benefits and are even perceived in some cases as irritating or to cause itching. This may be attributable, not only to the fact that some people are allergic to lanolin, but also as observed by Jacobi, et al., U.S. Pat. No. 3,231,472 dry skin is not caused by the loss of fat material in skin but by the loss of the water soluble constituents therein. In accordance with the present invention, a glucose glutamate condensation product of an amino acid with a reducing sugar is applied to a web of cellulosic fibers in an amount from 0.1 to 2% by weight of the web. The presence of small residual amounts of glucose glutamate on the skin, after hand drying, materially aids in restoring and maintaining the moisture balance necessary for healthy skin. This condensation product is disclosed and described in detail in U.S. Pat. No. 3,231,472, incorporated herein by reference. As will be readily appreciated, the fact that the polymers of the present invention are water-soluble totally distinguishes the treatment of the present invention from that of the lanolin treatments of the prior art. The high molecular weight polymers of the present invention are commercially available from Wickhen Products, Inc., a wholly-owned subsidiary of Dow Corning, under the brane name WICKENOL.

DETAILED DESCRIPTION

For the purpose of illustrating the present invention, paper webs having a basis weight of 54 g/m$^2$ (32 rounds per ream of 2,880 square feet) were treated in the finishing process at a point after the paper has been unwound from the parent roll and embossed, but before the slitting, folding, cut off stacking and wrapping processes. The treating fluid, comprising the active ingredients dissolved in water, is applied at a rate to yield the addition of between 0.034 to 1.086 g/m$^2$ (0.02 to 0.64 pounds per ream) of the WICKHEN compound or 0.1 to 2.0% by weight of the web. For toilet tissue such as Scott COTTONELLE or 2-ply facial, another example illustrating the present invention could be paper webs having basis weight of 27 g/m$^2$ (16 lbs. per ream) of 2,880 square feet were treated at location similar to that disclosed above. The treating fluid comprising the active ingredients dissolved in water is applied at a rate to yield an addition of between 0.017 to 0.543 g/m$^2$ (0.01 to 0.32 lbs./ream of the compound or 0.1 to 2% by weight of web.

Any application technique known in the art which does not unduly compact the web and which evenly distributes the fluid at the desired rate onto the paper web may be employed. These application techniques include spraying, transfer roll coating and gravure printing. If compaction caused by gravure printing is considered too great to the finished product, this step may be carried out prior to the step of bulking by embossing. The amount of compaction which can be suffered is influenced by numerous variables such as the original bulk of the web, consumer expectations regarding bulk and the perceived need for patterned printing which can be achieved by gravure roll methods. The present inventors have found that the benefits perceived by users are best achieved by spraying the treating fluid onto the web.

Two sheets were prepared as follows:

EXAMPLE 1

A paper web having a basis weight of 31.2 pounds per ream of 2880 square feet (52.9 grams per square meter) was sprayed on one side of the sheet with a Wickenol formulation containing 3.75% glucose glutamate in solution to yield a lotionized sheet containing 0.27% glucose glutamate by weight of the web.

EAMPLE 2

A paper web having a basis weight of 33.1 pounds per ream of 2880 square feet (56.2 grams per square meter) was sprayed on one side of the sheet with Alcolac lanolin (RRT-1-200A) containing 5% lanolin in solution to yield a lotionized sheet containing 0.27% lanolin by weight of web.

Towels fabricated from sheets made in accordance with the preceding examples 1 and 2 and a control towel were tested by a panel of nurses to evaluate the condition of their hands after repeated drying of their hands. Sensory perceptions are, of course, subjective; however, the results, it is believed, validly rank the towels in relation to one another. The testing procedure asked participants to compare the condition of their hands after four dryings with a control towel against four dryings with a test towel. The control towel consisted of untreated paper towels, commercially available as SCOTT Brand 150 C-fold towels. All test towels were kinder to participants' hands than the control towel, as evidenced by the percentage stating their hands felt the same or better after the dryings. The length of time it took to dry hands with the control towel and the test towels was the same. On average, the drying time was sixteen seconds. The testing procedure comprised a wash and dry sequence as follows: one wash and dry with control towel, followed by one with test towel; four wash and dry sequences with control towel followed by four with test towel; and finally five with test towel. In the test of towels made in accordance with Example 1 (Wickenol), at the end of the test 58% of the participants said their hands felt better, 17% said they felt the same and 25% said their hands felt worse. In the test of towels made in accordance with Example 2 (lanolin) at the end of the test,.27% of the participants said their hands felt better, 9% said they felt the same and 64% said their hands felt worse.

What is claimed is:

1. A method of simultaneously absorbing water or aqueous body fluids from the human skin while imparting to the skin an emollient effect by wiping the skin with a web of cellulosic fibers treated with an emollient composition consisting essentially of a water-soluble emollient, said emollient comprising glucose glutamate in an amount from 0.1 to 2% by weight of the web.

* * * * *